United States Patent [19]
Malmqvist et al.

[11] Patent Number: 5,965,456
[45] Date of Patent: *Oct. 12, 1999

[54] ANALYTE DETECTION

[75] Inventors: Magnus Malmqvist, Uppsala, Sweden; Gregory Paul Winter, Cambridge, United Kingdom

[73] Assignee: Biacore AB, Sweden

[21] Appl. No.: 08/848,175

[22] Filed: Apr. 29, 1997

Related U.S. Application Data

[63] Continuation of application No. 08/351,300, filed as application No. PCT/GB93/01242, Jun. 11, 1993, abandoned.

[30] Foreign Application Priority Data

Jun. 11, 1992 [GB] United Kingdom ............... 9212416

[51] Int. Cl.$^6$ ................................................. G01N 33/543
[52] U.S. Cl. .................. 436/514; 422/82.05; 422/82.11; 435/6; 435/7.1; 435/287.2; 435/287.9; 435/288.7; 435/808; 436/164; 436/501; 436/524; 436/525; 436/527; 436/528; 436/529; 436/805; 436/807; 436/824; 436/52
[58] Field of Search ............................. 422/82.05, 82.11; 435/6, 7.1, 287.2, 287.9, 288.7, 808; 436/501, 514, 524, 525, 527, 518, 528, 529, 52, 164, 805, 807, 824

[56] References Cited

FOREIGN PATENT DOCUMENTS 90 11525   10/1990   WIPO .
91 2981    3/1991    WIPO .

OTHER PUBLICATIONS

Choquette et al., "Planar Waveguide Immunosensor with Fluorescent Liposome Amplification," *Analytical Chemistry*, vol. 64, pp. 55–60 (1992).

Ward, et al: "Binding activities of a repertoire of single immunoglobulin variable domains secreted from *Escherichia coli*", Nature, vol. 341, Oct. 12, 1989, pp. 544–546.

Johnson, et al: "Real–Time Biospecific Intereaction analysis Using Surface Plasmon Resonance and a Sensor Chip Technology", Biotechniques, vol. 11, No. 5, Nov. 1991, pp. 620–627.

Karlsson, et al: Kinetic analysis of monoclonal antibody–antigen interactions with a new biosensor based analytical system:, Journal of Immunological Methods, vol. 145, 1991, pp. 229–240.

Anderson, et al: "Fiber Optic Immunochemical Sensor for Continuous, Reversible Measurement of Phenytoin". Clinical Chemistry, vol. 34, No. 7, Jul. 1988, pp. 1417–1421.

Johnsson, et al: "Immobilization of Proteins to a Carboxymethyldextran–Modified Gold Surface for Biospecific Interaction Analysis in Surface Plasmon Resonance Sensors", Analytical Biochemistrym vol. 198, No. 2, Nov. 1991, pp. 268–277.

Altschuh, et al: "Determination of Kinetic Constants for the Interaction between a Monoclonal Antibody and Peptides using Surface Plasmon Resonance", Biochemistry, vol. 31, No. 27, Jul. 14, 1992, pp. 6298–6304.

Griffiths, "Human anti–self antibodies with high specifity fro phage display libraries", EMBO Journal, vol. 12, No. 2, Feb. 1993, pp. 725–734.

O'Shannessy, et al: "Immobilization Chemistries Suitable for Use in the BIAcore Surface Plasmon Resonance Detector", Analytical Biochemistry, vol. 205, No. 1, Aug. 15, 1992, pp. 132–136.

*Primary Examiner*—Christopher L. Chin
*Attorney, Agent, or Firm*—Seed and Berry LLP

[57] ABSTRACT

Disclosed is apparatus for detecting the presence of an analyte of interest in a sample, comprising an immobilised binding partner comprising a solid support and a reversibly binding receptor which is capable of binding to the analyte of interest thereby causing a measurable change in a property of the immobilised partner, and detection means for detecting the measurable change and a method for detecting the presence of an analyte of interest.

10 Claims, 6 Drawing Sheets

ANALYTE DETECTION

This is a continuation of application Ser. No. 08/351,300, filed on Feb. 27, 1995, which was abandoned upon the filing hereof which is a 371 of PCT/GB93/01242 filed Jun. 11, 1993.

FIELD OF THE INVENTION

This invention relates to apparatus for analyte detection, particularly biosensors, and a method of detecting the presence of an analyte.

BACKGROUND OF THE INVENTION

Apparatus and methods for investigating the binding of analytes in solution to a receptor are known. One such apparatus (and its associated computer control and data-processing means) called BIAcore (BIAcore is a trademark of Pharmacia Biosensor AB; BIA stands for biospecific interaction analysis) has been devised, which uses the phenomenon of surface plasmon resonance (SPR) to study the binding of analytes to receptors immobilised on a sensor chip. The apparatus and theoretical background are fully described in the literature (e.g. Jönsson et al., 1991, Bio-Techniques 11, 620–627). Essentially, the technique involves the immobilisation of a receptor to the special surface of a sensor chip, contacting the chip with a flow of sample containing the analyte of interest, and then measuring the change in the surface optical characteristics of the sensor chip arising from the binding of the analyte of interest.

The specific nature of the antibody/antigen interaction means that such reactions are particularly amenable to investigation using the BIAcore system. For example J önsson et al. (1991, cited above) disclose the use of high affinity antibodies for concentration determinations. In this system the sensor chip required regeneration with HCl after each assay. There are several other reported studies which describe, for example, the interaction of synthetic peptides with immobilised monoclonal antibodies (Altschuh et al., 1992, Biochemistry 31, 6298–6304), and binding reactions between immobilised monoclonals and HIV core protein p24 and vice versa; Karlsson et al., 1991, Journal of Immunological Methods 145, 229–240).

Sensors for applications such as on-line monitoring of chromatography, fermentation or even in vivo use, should ideally give rapid, reversible and sensitive responses to changes in concentrations of proteins or other biomolecules. Normally antibodies have strong binding of antigen and can only be used as monitor of the concentration as a dosimeter. For such applications regeneration of the antibody (to recreate vacant antigen-binding sites), or the use of disposable items is required. However, in many environments regeneration with chemical agents can not be done.

It is apparent from the prior art that for an antibody-based solid-phase biosensor to be capable of measuring reversibly (without the need for regeneration), the antibody should have a high dissociation rate constant in binding antigen ("k off") (Anderson & Miller, 1988, Clinical Chemistry 34, 1417–1421) but those authors do not disclose antibodies or fragments thereof having intrinsically high dissociation rate constants for continuous on-line sensing.

However, there are considerable difficulties in actually obtaining receptor molecules (such as antibodies) with the desired properties. This is because virtually all screening methods for searching for suitable candidate molecules require a washing step. Such a washing step would tend to remove the very molecules possessing the properties for which one was screening.

Thus, all of the prior art disclosures regarding biosensors relate to the use of "mature" monoclonal antibodies produced as a result of the primary immunisation and subsequent boosting of the relevant laboratory animal (typically, a mouse). These antibodies therefore bind antigen too strongly for the reaction to be readily reversible. Moreover, these antibodies are typically directed against haptens. The shortest reversible response time reported (Anderson & Miller, above) was in the range 5–15 minutes (for the comparatively high analyte concentration range of 5–100 mM), which is not quick enough to follow parameters for many "on-line/real-time" applications. Further, the apparatus disclosed therein required the use of dialysis tubing. This results in severe limitations on the molecular weight of analytes that may be studied.

SUMMARY OF THE INVENTION

In a first aspect the invention provides apparatus for detecting the presence in solution of an analyte of interest in a sample, comprising an immobilised binding partner comprising a solid support and a reversibly binding receptor which is capable of binding to the analyte of interest thereby causing a measurable change in a property of the binding partner, and detection means for detecting the measurable change.

In another aspect, the invention provides a method of detecting the presence of an analyte of interest in a sample, comprising contacting the sample with apparatus in accordance with the first aspect, and detecting a measureable change in a property of the binding partner, responsive to binding of the analyte to the binding partner.

For the purposes of the present specification, a reversibly binding receptor has a dissociation rate constant (K off), (for a particular analyte of interest) of greater tnan $10^{-2}$ per second and the half-life of the receptor/analyte complex is less than or equal to approximately 60 seconds.

The reversibly binding receptor is preferably a whole antibody, or may be a fragment thereof, such as an Fab fragment, an Fv fragment, a single chain Fv fragment (scFv), a single heavy chain or even a peptide (based on the nucleotide sequence of antibody gene) having binding activity. Other examples are "Diabodies" (polypeptides with bifunctional or bivalent binding characteristics (as disclosed by Winter, 1993, Current Opinion in Immunology 5, 253–255), where one or both binding sites may possess the necessary reversible binding characteristics). The reversibly binding antibody may also possess a non-immunoglobulin region such as a fusion protein in which other domains of the molecule could be used, for example, to bind to the solid support or have another function for the signal transformation to the transducer.

Alternatively, the reversibly binding receptor may be wholly non-immunoglobulin in nature. For example, the receptor could be a peptide (with no structural similarity to immunoglobulins; e.g. Lam et al. 1991 Nature 354, 82–84; Houghten et al. 1991 Nature 354, 84–86) or even a nucleotide sequence (e.g. Tuerk & Gold, 1990 Science 249, 505–510).

Consider a reversible reaction between a reversibly binding receptor (such as an antibody "Ab") and an antigen "Ag" (being an analyte of interest) as having two rates of reaction: a forward "on" rate constant ($K_1$) and a backward "off" rate constant ($K_2$).

The reversibly binding receptors of the apparatus of the present invention have surprisingly high "off" (dissociation) rate constants. For example, where the reversibly binding receptor is an antibody (or a fragment thereof), such molecules will typically not have undergone affinity maturation.

The very high dissociation rate constants mean that where the receptors are used to detect the presence of an analyte of interest, should the concentration of the analyte fall, the immobilised receptor will readily become dissociated from the analyte, allowing the apparatus of the invention to rapidly respond to changes in analyte concentration. The invention is, as a result, perfectly suited for "on-line", "real-time" measurement of changing parameters, and may be used quantitatively or qualitatively.

Antibodies or antibody fragments suitable for use in the apparatus of the present invention may be obtained from hybridomas or most preferably from V-gene repertoires. The repertoires can be provided from libraries of rearranged V-genes (ward et al., 1989, Nature 341, 544–546; Huse et al., 1989 Science 246, 1275–1281) from the lymphocytes of immunised (Huse et al., 1989; Clackson et al., 1991 Nature 352, 624–628), or unimmunised (Marks et al., 1991 J. Mol. Biol. 222, 581–597) humans or animals. Repertoires of single antibody domains could be used (Ward et al., 1989), or repertoires of associated VH and VL domains by randomly recombining repertoires of VH and VL genes (Huse et al., 1989 cited above). Alternatively antibody V-genes could be rearranged in vitro (Hoogenboom & Winter, 1992, J. Mol. Biol. 227, 381–388) from V-gene segments and synthetic (random) hypervariable loops. The repertoires of encoded antibody fragments could be secreted from bacteria and screened by binding to antigen (e.g. Ward et al., 1989 cited above; Huse et al., 1989 cited above). The repertoires could also be encoded for display on the surface of filamentous bacteriophage, and phage with binding activities selected by binding to antigen (McCafferty et al., 1990, Nature 348, 552–554; Marks et al., 1991, cited previously).

Whether the antibody binding specificities are derived from hybridomas or from gene repertoires, by screening or selection, it is necessary to contact the antibodies with antigen, and almost always necessary to follow this with a washing step. Since the desired antibodies have a fast dissociation rate, it is necessary to prolong the interaction with antigen. This can be achieved by making multivalent interactions, for example by binding the bivalent IgG or pentavalent IgM of hybridoma supernatants, or the multivalent phage particles, to solid phase antigen coated at high density. The antibodies, or phage antibodies therefore bind with a higher avidity than each of the single antibody heads alone. Altnernatively, even with monovalent interactions, for example using Fab fragments, by coating the solid phase at high density of antigen, the fragments that dissociate can rebind to the surface. In this way monomeric fragments with fast dissociation kinetics can be identified despite the washing step, either by taking advantage of multivalency or by promoting rebinding, such that the net rate of dissociation of the receptor/antigen complex is reduced (where the antigen is, or is closely similar to, the analyte to be detected by the receptor).

Yet another approach would be to alter or "engineer" the existing genes for an antibody or antigen-binding antibody fragment so as to introduce the desired characteristics. Such alterations would probably include changes in the CDRs of the variable region but might also involve changes in the frameworks. Such alterations could be introduced by known methods (e.g. site-directed mutagenesis). Whilst it is not immediately apparent what amino acid residues should be altered to produce the desired characteristics, it should not be beyond the skill of the average man, using trial and error, to engineer appropriate alternatives.

Preferably the reversibly binding receptors are antibodies or antigen binding fragments directed against "conventional" polypeptide antigens rather than hapten antigens.

It will be apparent to those skilled in the art that the apparatus of the present invention can form the basis of a biosensor. Preferably, the apparatus is associated with the relevant instruments and computer control and data-processing means for performing assays. Suitable instrumentation, computer control and data-processing means are well known (e.g. the BIAcore System, Pharmacia Biosensor AB).

Preferably the property of the immobilised binding partner which undergoes a measurable change is an optical property. Most preferably the property is the surface refractive index, although other detection means are known based, for example, on measurement of: electrical, electrochemical or piezoelectrical properties; evanescent wave-based refractometry, evanescent wave-based imaging; transmission-based refractometry; or surface acoustic wave (SAW) measurement.

It is found that preferred embodiments of the apparatus of the invention are able to detect quantitatively an analyte in the concentration range 10–200 nM. Further, it is found that preferred embodiments of the invention have a reversible response time of about 25 seconds, significantly quicker than that of the most rapid apparatus described in the prior art (Anderson & Miller, 1988, cited above).

Preferably the detection means involves the use of Surface Plasmon Resonance (SPR) to detect the binding of analyte to the immobilised binding partner e.g. as with the BIAcore apparatus.

The various aspects of the invention will now be further described with reference to the following illustrative examples and drawings, of which:

EXAMPLES AND DETAILED DESCRIPTION OF THE DRAWINGS

Figure 1A:
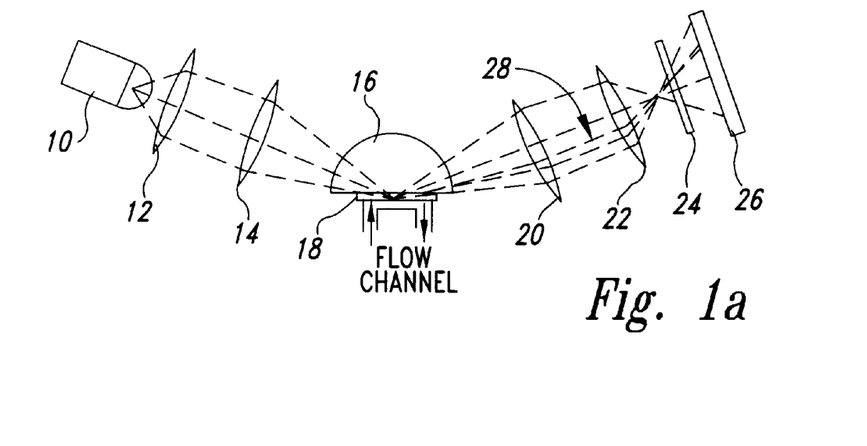
FIG. 1a shows a schematic side view.

FIG. 1a shows schematically in side view one embodiment of apparatus in accordance with the invention. Light emitted by a light emitting diode (LED) 10, passes through a collimator 12, a focussing lens 14 and a prism 16, before striking a sensor chip 18. Due to the large angle of incidence, the light undergoes total internal reflection, exits the prism 16 and then passes through an objective lens 20, a cylindrical lens 22, and a plane polarizer 24, before striking a photodetector 26. The system allows for a range of incident angles (66–69°) and the photodetector enables changes in the reflection angle to be monitored as a function of time. Arrow 28 points to the hypothetical light path of the reflectance minimum. The apparatus also comprises computer control and data-processing means (not shown).

Figure 1B:
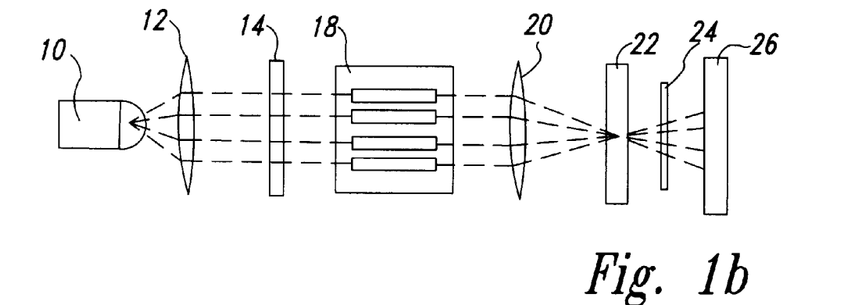
FIG. 1b shows a schematic plan view of one embodiment of apparatus in accordance with the invention.

The same embodiment is shown schematicaly in plan view in FIG. 1b. The apparatus is more fully described by Jönsson et al., (referred to above).

Figure 2:
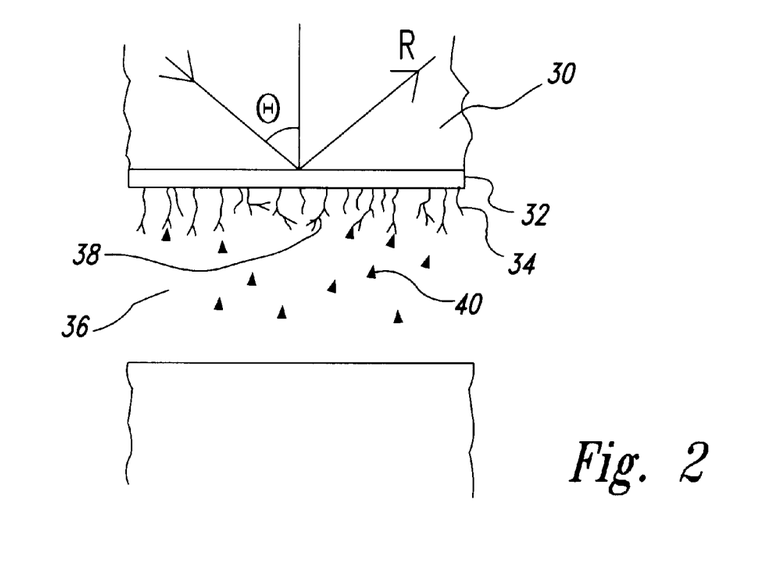
FIG. 2 shows an enlarged schematic side view of part of the apparatus shown in FIG. 1.

FIG. 2 illustrates schematically the interface between the sensor chip (18 in FIGS. 1a, 1b) and the flow channel. The sensor chip 18 acts as an immobilised binding partner comprising a glass support 30 coated with a thin (47 nm±15 nm) gold film 32. A flexible hydrophilic polymer (e.g. dextran) 34 is bound to the gold film 32 and extends about 100 nm (depending on buffer conditions) from the gold film 32 into the flow channel 36. An antibody 38 is coupled to the flexible hydrophilic polymer 34 by standard chemistry. Thus the immobilised binding partner of the apparatus comprises the solid support 30 and the antibody 38. The antibody is capable of interacting with an analyte of interest 40 in the sample passing through the flow channel 36. Angle $\theta$ shows the angle of incident light. R is the reflected ray.

To demonstrate the utility of the present invention, a number of experiments were performed using apparatus similar to that described above. These were essentially of two types. One group of experiments used a recombinant antibody fragment immobilised on a sensor chip to detect different concentrations of an antigen bound by the antibody fragment.

A second group of experiments used antigens immobilised on a sensor chip to detect the binding (and release) of recombinant naive antibody fragments passing the sensor as effluent from a gel filtration column, compared with the behaviour of a "mature" monoclonal antibody fragment.

The first group of experiments were performed to demonstrate the utility of antibody fragments in effective "real-time" immunosensing.

Affinity-purified anti-Fog-1 scFv (938 RUs) was immobilised on a CM5 sensor chip using the amine coupling kit using a solution of about 3 uM in 10 mM acetate buffer (pH4.5). Human IgG1 Kappa (bearing the Fog-1 antigen), at concentrations in the range 10–200 nM in elution buffer, was run over immobilised anti-Fog-1 scFv in 5 cycles for each concentration without intervening regeneration. Analysis with the BIAcore system was performed in PBS 0.2 mM EDTA/0.05% surfactant P20 (Pharmacia Biosensor AB) at 10 ul/min.

Figure 3:
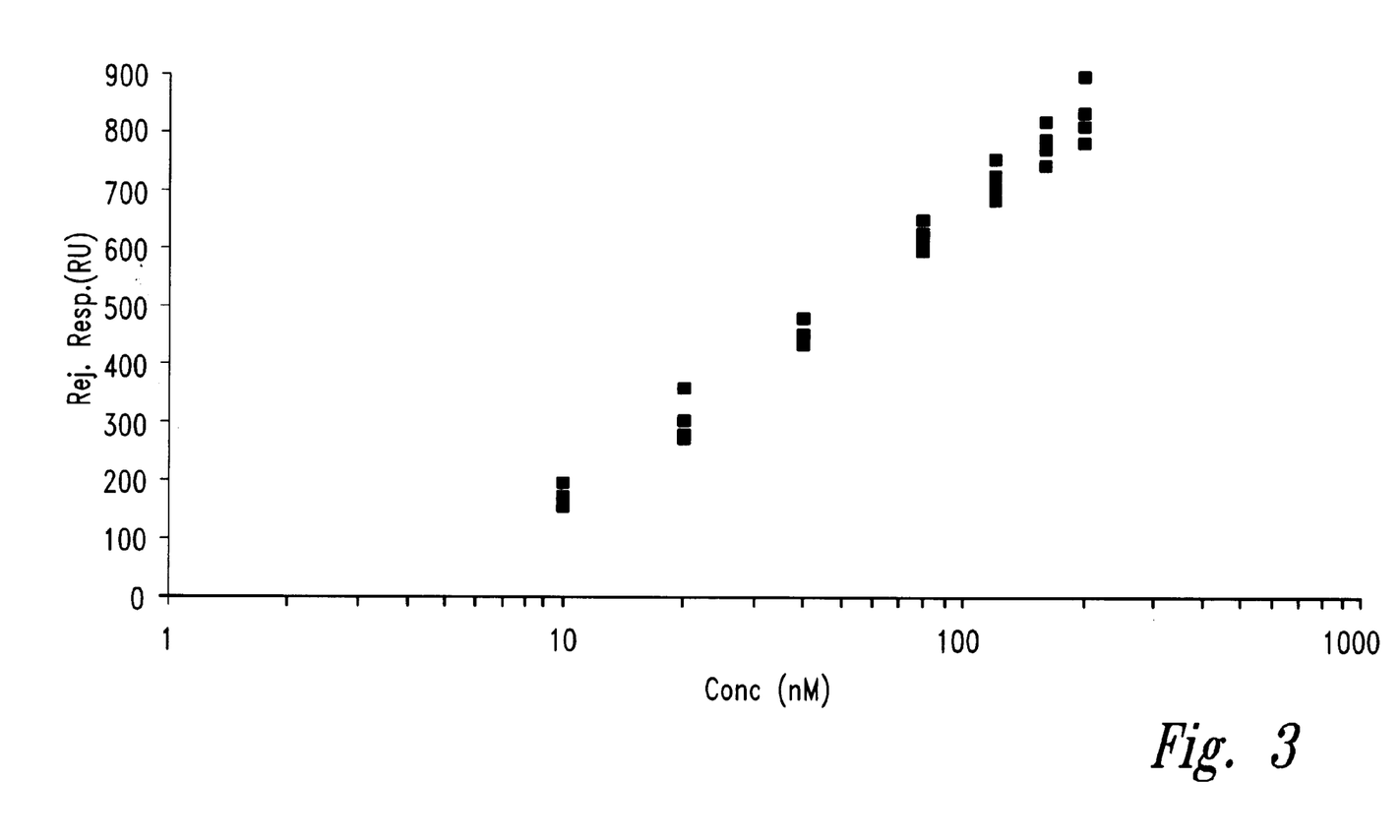
FIG. 3 shows a dose/response curve of response against concentration in an assay using the apparatus and method of the invention.

The response level reached 25 seconds after the injection of each sample was plotted in a dose/response curve. The results are shown in FIG. 3. The graph shows a reasonably straight line demonstrating that under the conditions employed, the response was proportional to the concentration of antigen and that this proportionality may indeed extend over a greater concentration range.

To illustrate the rapidity of the response, the same concentrations of antigen were run over the immobilised anti-Fog-1 by sequential injections in manual mode (by queuing the command). The injections were thus done as fast as the subroutines (for needle wash and loop filling) can be processed by the BIAcore system. The concentration series was 200, 10, 40, 20, 160, 80 and 120 nM. The time delay between sequential injections was 130 seconds. The same samples were also run over a bare CM5 chip as a control (thin trace).

Figure 4:
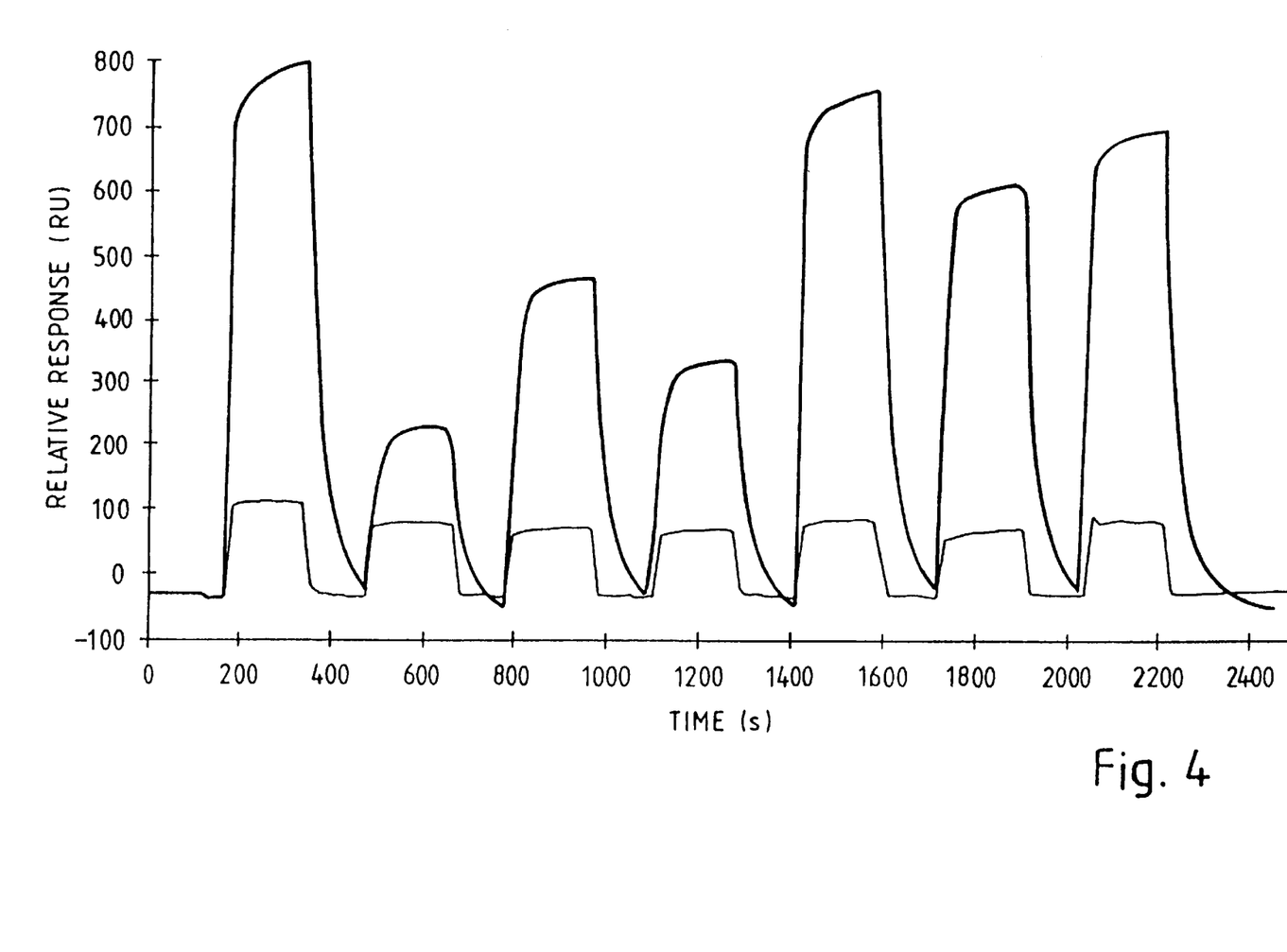
FIG. 4 shows a graph of relative response against time.

The results are shown in FIG. 4, which is a graph of response (RU) against time (seconds).

It can be seen from the graph that for each concentration in the series, the response has returned to the baseline before the next concentration of antigen is injected. This means that BIAcore is the limiting factor in rapid, reversible, semi-continuous concentration determinations.

The second group of experiments analysed the effect of different affinity in the on-line gel filtration sensorgrams of two different recombinant antibody fragments: a low affinity scFv against the hapten 2-phenyloxazol-5-one (phOx), derived from a synthetic gene library (described by Hoogenboom & Winter (1992) J. Mol. Biol. 227, 381–388); and an scFv derived from a naive library (described by Griffiths et al., (1993), EMBO J. 12, 725–734) directed against Fog-1 (which is a human IgG 1 Kappa antigen). Their behaviour was compared with that of an scFv derived from a 'mature' monoclonal antibody (MAb) D1.3 (directed against hen egg lysozyme, HEL).

The experiments were performed as set out below, and demonstrate the importance of avidity effects.

FPLC equipment (Pharmacia-LKB Biotechnology AB, Uppsala, Sweden) was positioned as close as possible to BIAcore apparatus (Pharmacia Biosensor AB, Uppsala, Sweden) generally as described above and the outlet from the UV detector was connected to the pump tube inlet in the autosampler connector block. A 0.5 mm stainless tube was connected to the drain from the flow cell so the effluent could be collected in a fraction collector. A Superdex 75 FPLC column 1.0×30 cm was used in PBS 0.2 mM EDTA with a flow rate of 0.5 ml/min. In order to avoid damage to the integrated fluidics (IFC) in the BIAcore apparatus no higher flow rates were used. The distance from outlet of the UV monitor and inlet to the BIAcore apparatus was approximately 15 cm. Manual sensorgrams on the BIAcore apparatus were run and presentations were made in Excel software (FIGS. 5–6b).

The relevant antigens were immobilised on a CM5 sensor chip by use of the amine coupling kit (obtained from Pharmacia Biosensor AB, described by Jönsson et al., (1991) Analytical Biochemistry 198, 268–277). The hapten phOx was conjugated to BSA, the resulting antigen coupled to the sensor following the method described by Marks et al. (1992, Bio/Technology 10, 779–783) to a level of about 1300 relative resonance units (RU) and hen egg lysozyme coupled to a level of about 800 RU, using a 20 ug/ml solution of HEL in 10 mM acetate buffer pH5.0.

Size calibration of the column was performed by using the column to separate a mixture of BSA, ovalbumin and HEL each having an OD of 0.5, and detected by refractive index change in the column effluent using the BIAcore apparatus.

Figure 5:
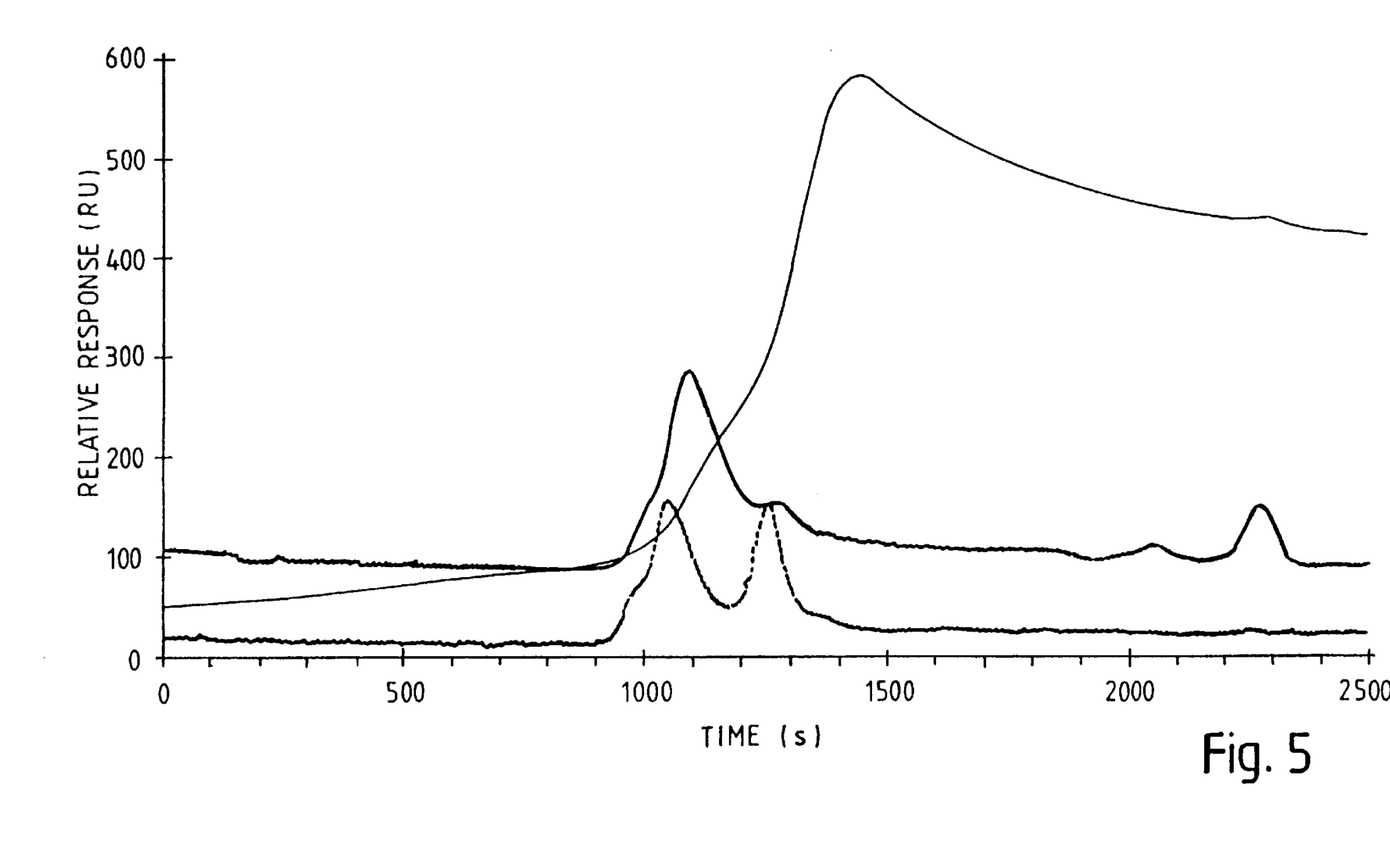
FIG. 5 shows three traces on a graph of relative response against time for the detection of recombinant antibody fragments by a sensor with immobilised antigen.
Figure 6A:
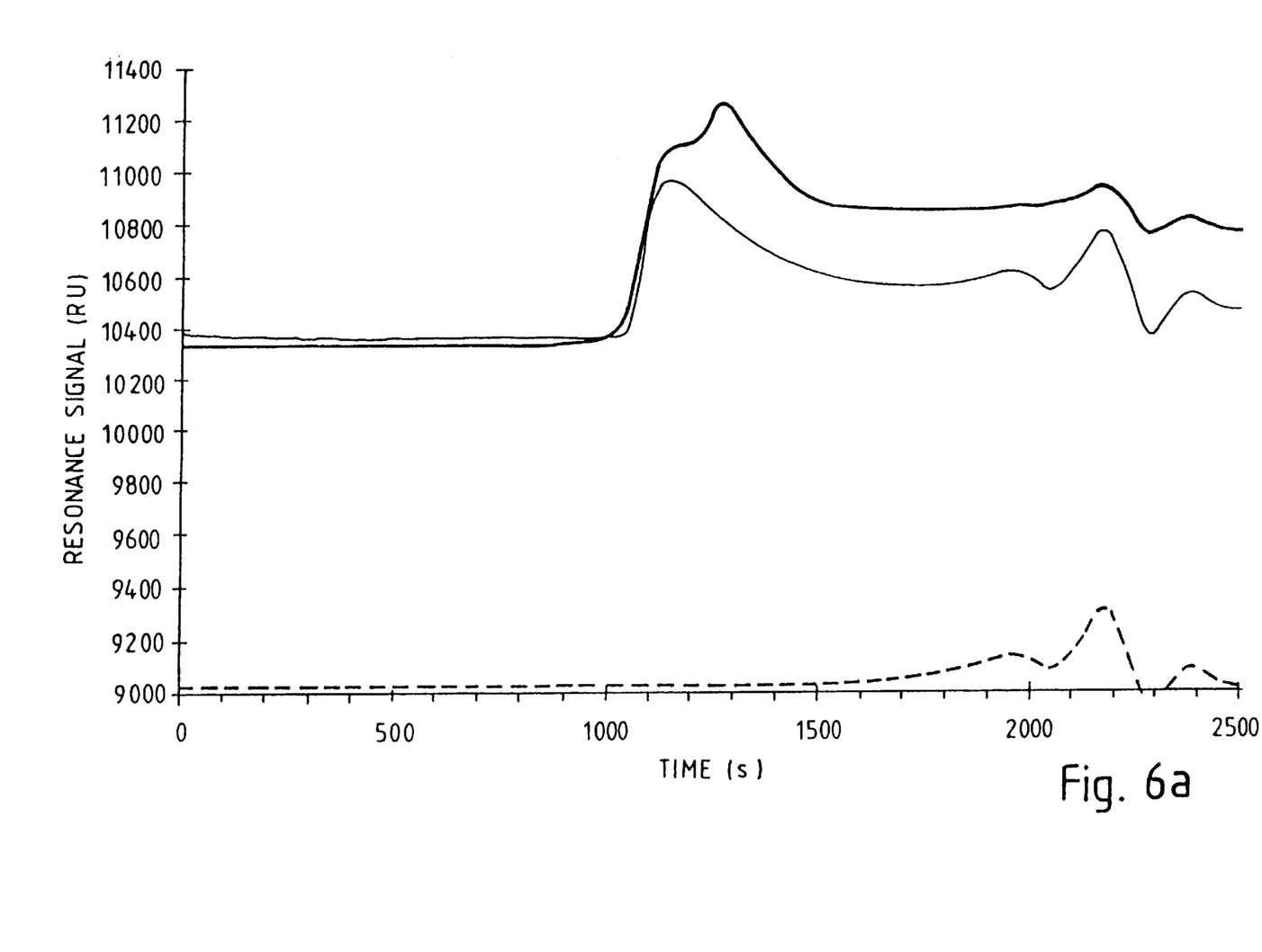
FIG. 6a shows three traces on a graph of resonance signal against time.
Figure 6B:
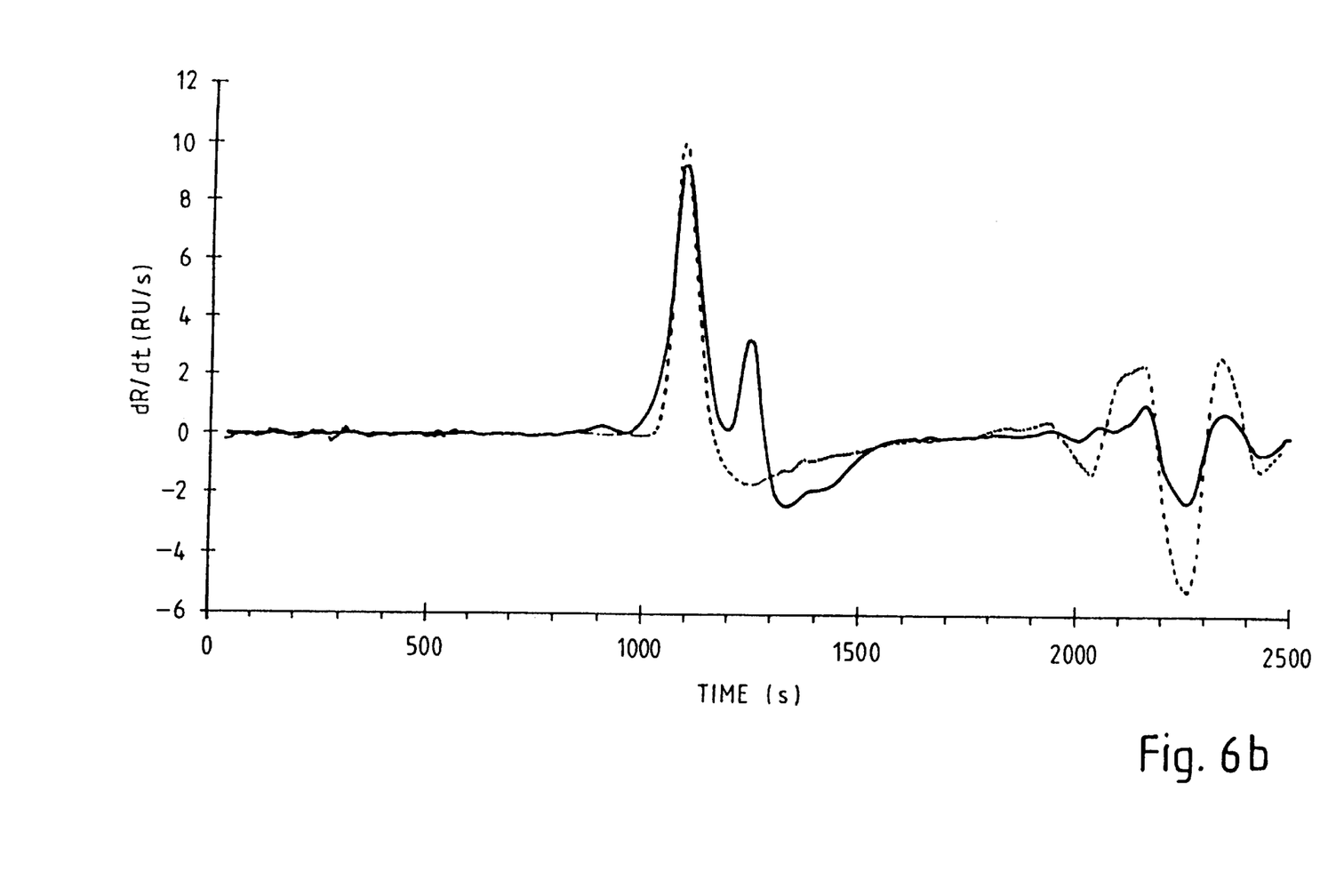
FIG. 6b shows two traces on a graph of rate of change of resonance signal (dR/dt) against time.

The results of the first of this second group of experiment are shown in FIG. 5, which shows how different affinity and Kinetic constants affect the response using the BIAcore System.

FIG. 5 is a graph of relative resonance units (RU) against time (in seconds). There are three traces, showing the specific response due to binding of the antibody fragments in gel filtration effluents to CM5 chips coated with the appropriate antigen. The thin line shows the trace for binding of affinity-purified scFv of D1.3 (the "mature" anti-HEL antibody). (This scFv was purified by affinity chromatography from supernatant with the immobilised antibody 9E10 using the C-terminal myc-tag, as described by Clackson et al., [1991], Nature 352, 624–628). The lowest (dotted line) trace is that for binding of the anti-phOx scFv clone 31, and the thickest trace is that for binding of the anti-Fog-1 ScFv. The results show that all three scFv fragments had aggregated to some extent and that adsorption of scFv fragments occurred at time points corresponding to elution of scFv monomers and dimers. The high affinity D1.3 scFv was adsorbed to the antigen surface during elution of both dimers and monomers but the other two scFv fragments had much higher dissociation rates after the passage of the dimer peak and were adsorbed again at the point corresponding to elution of the monomers.

To prove the specificity of the on-line detection with the BIAcore instrument, two recombinant antibody fragments against phOx in growth media were subjected to gel filtration. One scFv, termed B2, was derived from a library by chain shuffling, (Marks et al. 1992, cited above). The other was an Fab fragment labelled NQ10, derived from a high affinity MAb, used as a size marker.

Growth culture supernatant containing the scFv B2 was concentrated five-fold by ultrafiltration on Centricon 10 concentrators (Amicon). The Fab fragment NQ10 was obtained directly from culture supernatant.

The two gel filtration effluents were run over both an antigen-coated chip and a bare CM5 sensor chip surface. No adsorption from the void volume was seen on the antigen chip nor was any material adsorbed on the bare CM5 surface. However, peptides and other coloured substances gave rise to refractive index changes in later parts of the separation both in the specific detection and in the control run. These results are illustrated graphically in FIGS. 6a and 6b. FIG. 6a is a graph of Resonance Units against time (in seconds). FIG. 6b is a graph of rate of change of resonance signal (RUs per second) against time (in seconds).

FIG. 6a shows the on-line specific binding of anti-phOX (B2) scFv (thick trace) and anti-phOX NQ10 Fab fragment (thin trace) to a phOX-BSA coated surface detected by the BIAcore apparatus. Both antibodies in growth medium were separated on Superdex 75. The dotted trace at the bottom of the graph shows the trace given by NQ10 in growth medium run over an uncoated CM5 sensor chip surface.

The NQ10 Fab and dimer of the B2 were eluted at the same position and the monomer of scFv B2 can be seen as an extra peak in the sensorgram. The dissociation of Fab NQ10 from the antigen surface has the shape of a logarithmic decay in the position from the peak to the elution of small peptides and other nutrients from the medium (at T=2,000–2,500). This is in contrast to dissociation profile for B2, which exhibits mixed dissociation with a rapid decay of the monomer scFv (due to its reversible binding properties) and a slow dissociation seen from about 1500 s. This might be the result of stabilisation of the B2 dimers binding to the haptenised BSA by two binding sites.

FIG. 6b shows the derivative of the signal (dR/dt) given in FIG. 6a for scFv B2 (solid line) and NQ10 Fab (broken line). The maximal association rates are at the same elution position for both dimeric B2 and NQ10 Fab, with another peak corresponding to the elution of monomeric B2 (based on the calibration with the albumin, ovalbumin and lysozyme standards). The rapid dissociation of the scFv monomer is seen as a large negative value.

We claim:

1. An apparatus for detecting the presence of an analyte of interest in a solution sample, comprising:

an immobilized binding partner comprising a solid support and a reversibly binding receptor which is capable of binding to the analyte of interest, such binding forming a receptor/analyte complex and thereby causing a measurable change in a property associated with the immobilized binding partner; and a detection means for detecting the measurable change, wherein the receptor/analyte complex has a dissociation rate constant of greater than $3.2 \times 10^{-2}$ per second such that the apparatus responds rapidly to changes in analyte concentration and is suitable for on-line, real time measurement of the analyte.

2. The apparatus according to claim 1, wherein the reversibly binding receptor is an antibody or an antigen-binding fragment thereof, a peptide or a nucleotide sequence.

3. The apparatus according to claim 2, wherein the reversibly binding receptor is an antibody or an antigen-binding fragment thereof comprising a polypeptide sequence encoded by a nucleotide sequence obtained from a V gene repertoire.

4. The apparatus according to claim 2, wherein the reversibly binding receptor is an antibody or an antigen-binding fragment thereof derived by selection from a library using a phage display method.

5. The apparatus according to claim 2, wherein the reversibly binding receptor comprises a single chain variable region fragment (scFv).

6. The apparatus according to claim 2, wherein the apparatus is capable of detecting quantitatively an analyte of interest in a concentration range of 10–200 nM.

7. The apparatus according to claim 2, wherein the reversibly binding receptor is an antibody or an antigen-binding fragment thereof which binds a polypeptide antigen.

8. A method of detecting the presence of an analyte of interest in a sample, comprising contacting the sample with the apparatus according to claim 1, and detecting a measurable change in a property associated with the binding of the reversibly binding receptor to the analyte of interest.

9. The method according to claim 8, comprising on-line qualitative or quantitative detection of an analyte of interest.

10. The apparatus according to claim 1 having a reversible response time of about 25 seconds.

* * * * *